(12) United States Patent
Sayegh (10) Patent No.: US 9,421,128 B2
(45) Date of Patent: Aug. 23, 2016

(54) POSITIONING DEVICE FOR EYE SURGERY AND PROCEDURES

(71) Applicant: Samir Sayegh, Champaign, IL (US)

(72) Inventor: Samir Sayegh, Champaign, IL (US)

( * ) Notice: Subject to any disclaimer, the term of this patent is extended or adjusted under 35 U.S.C. 154(b) by 438 days.

(21) Appl. No.: 13/967,133

(22) Filed: Aug. 14, 2013

(65) Prior Publication Data

US 2014/0052140 A1    Feb. 20, 2014

Related U.S. Application Data

(60) Provisional application No. 61/682,770, filed on Aug. 14, 2012.

(51) Int. Cl.
| | | |
|---|---|---|
| *A61F 9/00* | (2006.01) | |
| *A61F 9/007* | (2006.01) | |
| *A61B 17/02* | (2006.01) | |
| *A61B 17/34* | (2006.01) | |

(52) U.S. Cl.
CPC .............. *A61F 9/007* (2013.01); *A61B 17/0231* (2013.01); *A61B 2017/3407* (2013.01)

(58) Field of Classification Search
CPC ..... A61F 9/007; A61F 9/013; A61B 17/0231; A61B 2017/3407
See application file for complete search history.

(56) References Cited

U.S. PATENT DOCUMENTS

| | | | | |
|---|---|---|---|---|
| 4,406,285 A | * | 9/1983 | Villasenor | A61F 9/0136 33/1 B |
| 4,688,570 A | * | 8/1987 | Kramer | A61F 9/013 606/166 |
| 4,844,060 A | * | 7/1989 | Krumeich | A61F 9/013 606/166 |
| 5,021,057 A | * | 6/1991 | Byrne, Jr. | A61F 9/007 606/107 |
| 5,354,331 A | * | 10/1994 | Schachar | A61F 2/147 424/427 |
| 5,876,415 A | * | 3/1999 | Pierce | A61F 9/013 606/166 |
| 5,951,579 A | | 9/1999 | Dykes | |

(Continued)

FOREIGN PATENT DOCUMENTS

EP    1099432 A    5/2001

OTHER PUBLICATIONS

Allen C. Ho, Microincision Vitrectomy Surgery Technique Evolves, Ophthalmology Times, Jun. 15, 2011, available at http://ophthalmologytimes.modernmedicine.com/ophthalmologytimes/news/modernmedicine/modern-medicine-feature-articles/microincision-vitrectomy-sur (last retrieved Oct. 21, 2013).

(Continued)

*Primary Examiner* — Kristen Matter
(74) *Attorney, Agent, or Firm* — Wendy Thai (57) ABSTRACT

The invention provides a positioning device for use in an examination, procedure or surgery of the eye. The positioning device includes an incurvate body with an upper peripheral edge having a first arc length, a lower peripheral edge having a second arc length, and a curved lateral portion therebetween. The lower peripheral edge has an arc length that is longer than the first arc length, as well as one to eight indentations of a size effective to receive a surgical instrument. The incurvate body of the positioning device of the invention is configured to engage at least a portion of the eye posterior to the corneal limbus and beneath which the pars plana is located. The positioning device can also include a handle pivotably attached to the incurvate body. The positioning device can be used to stabilize the eye as well as assist in accurate positioning of instruments during eye examination, procedure or surgery involving the anterior or posterior segment of the eye.

20 Claims, 5 Drawing Sheets

(56) References Cited

U.S. PATENT DOCUMENTS

| | | | | |
|---|---|---|---|---|
| 7,824,372 | B1* | 11/2010 | Kurup | A61F 9/0017 604/116 |
| 2002/0120285 | A1 | 8/2002 | Schachar et al. | |
| 2004/0267294 | A1 | 12/2004 | Will | |
| 2005/0288697 | A1* | 12/2005 | Tei | A61B 17/3403 606/166 |
| 2006/0136022 | A1* | 6/2006 | Wong, Jr. | A61B 3/165 607/104 |
| 2007/0088352 | A1* | 4/2007 | Rosen | A61B 18/1402 606/45 |
| 2008/0091224 | A1* | 4/2008 | Griffis | A61F 9/007 606/166 |
| 2010/0137780 | A1* | 6/2010 | Singh | A61B 17/0231 604/20 |
| 2013/0060254 | A1 | 3/2013 | Juhasz et al. | |
| 2014/0158139 | A1* | 6/2014 | Sayegh | A61B 17/0231 128/845 |

OTHER PUBLICATIONS

Ashraf M El-Batarny, Transconjunctival Sutureless 23-gauge Vitrectomy for Vitreoretinal Diseases: Outcome of 30 Consecutive Cases, Middle East Afr J Ophthalmol. 15(3): 99-105, Jul.-Dec. 2008, available at http://www.ncbi.nlm.nih.gov/pmc/articles/PMC3040921/ (last visited Oct. 22, 2013).

Helmut Kapczynski, Surgical Instruments 101: An Introduction to KMedic Certified Instruments, 1997, KMedic, Northvale, NJ, available at http://www.teleflex.com/en/usa/pdf/KMedic_Surgical_instruments_101.pdf (last visited Oct. 22, 2013).

Highlights from the Advanced Vitreoretinal Techniques & Technology Symposium in Hong Kong, Retina Today, Sep./Oct. 2008, available at http://www.retinatoday.com/issues/0908/0908_supp.pdf (last visited Oct. 22, 2013).

Lemley, C.A. & Han, D.P., An Age-based Method for Planning Sclerotomy Placement During Pediatric Vitrectomy: A 12-Year Experience, Trans. Am. Ophthalmol. Soc. vol. 105, p. 86-91 (2007) (available at http://www.ncbi.nlm.nih.gov/pmc/articles/PMC2258105/pdf/1545-6110_v105_p086.pdf).

Randy Pell, Surgical Instruments: Converting from Metal to Plastic, Medical Device & Diagnostic Industry, Oct. 2006, Canon Communications, 2006, available at http://www.mack.com/resource/MDDI_Oct06_RPell.pdf (last visited Oct. 22, 2013).

Rhein Medical, Quick View Ophthalmic Surgical Instruments Available from Rhein Medical, 05-7001 Fine Crescent Fixation Ring, p. 32, Nov. 27, 2012, available at http://www.rheinmedical.com/wp-content/uploads/2012/11/QuickView1248gWEB.pdf.

Rhein Medical, Quick View Ophthalmic Surgical Instruments Available from Rhein Medical, 05-7008 Seibel Gravity Fixation Ring, p. 59, Nov. 27, 2012, available at http://www.rheinmedical.com/wp-content/uploads/2012/11/QuickView1248gWEB.pdf.

* cited by examiner

POSITIONING DEVICE FOR EYE SURGERY AND PROCEDURES

CROSS-REFERENCE TO RELATED APPLICATIONS

This application claims priority to U.S. provisional patent application Ser. No. 61/682,770, filed Aug. 14, 2012, the contents of which is incorporated herein by reference in its entirety.

BACKGROUND

The eye is a complex assembly of various tissues that together function to receive and transmit light to the brain to enable vision. Eye function can deteriorate over time due to age, injuries, infections or various disease conditions resulting in impaired vision. Numerous procedures have been developed to treat various eye defects and conditions so as to improve vision. These include, for example, cataract surgery, refractive surgery including LASIK, trabeculectomy, vitreoretinal surgery, and intravitreal injection of pharmaceuticals. These eye procedures involve repeat placement, removal and exchange of various instruments, which must be accomplished with care, accuracy and precision while stabilizing the eye in order to avoid inadvertent incising of unintended ocular tissues.

In vitreoretinal surgery, for example, a trocar system is used through which instruments are introduced and exchanged throughout the procedure. Introduction and removal of the trocars during this procedure involve: (1) stabilizing the eye; (2) determining the correct trocar position in pars plana so as to avoid causing trauma to the natural lens or injury to the retina resulting in tears that can lead to retinal detachment; (3) dragging of the conjunctiva to achieve misalignment of entry points in conjunctiva and sclera; (4) removal of blade introducing the trocar; and (5) positioning the irrigation cannula. These steps are performed using multiple instruments that are exchanged during each step and for each sclerotomy—in the most common three-port pars plana vitrectomy surgery, these steps are repeated three times. As proper completion of these preliminary steps is crucial to initiating eye procedures in a safe and efficient manner, a great deal of time is taken to perform these steps, which therefore, account for a significant portion of the time involved in the procedure.

Furthermore, certain eye procedures do not require administration of regional anesthesia (its use can cause discomfort, bleeding or infection), movement of the eye, which can occur if no regional anesthesia is used, can interfere with proper placement, use and removal of various instruments thereby presenting a stability and safety issue.

SUMMARY

The invention provides a positioning device that can be used during eye exams, procedures or surgeries to assist in stabilizing the eye and/or for placement of various instruments so as to improve efficiency, accuracy, precision and/or safety. The positioning device includes a incurvate body having an upper peripheral edge with a first arc length, a lower peripheral edge with a second arc length longer than the first arc length, and a curved lateral portion disposed therebetween, the device having one to eight indentations on its lower peripheral edge. The upper peripheral edge, curved lateral portion and lower peripheral edge are configured to engage at least a portion of the eye that is posterior to the corneal limbus and beneath which the pars plana is located. The positioning device can include a handle pivotably attached to the upper peripheral edge for ease of use.

In one aspect, the invention provides a positioning device for use in an eye procedure that includes an incurvate body having (a) an upper peripheral edge with a first arc length, (b) a lower peripheral edge with a second arc length that is longer than the first arc length, the lower peripheral edge having one to eight indentations of a size effective to receive a surgical instrument, and (c) a curved lateral portion therebetween. The incurvate body is configured to engage at least a portion of the eye posterior to the corneal limbus and beneath which the pars plana is located.

In some embodiments, the curved lateral portion of the positioning device has an angle of about 40° to about 55° relative to a line normal to a plane parallel to the upper and lower edges. In some embodiments, the curved lateral portion of the positioning device has an angle of about 45° to about 49° relative to a line normal to a plane parallel to the upper and lower edges.

In some embodiments, the incurvate body is a frustoconical ring having a circular upper peripheral edge with a first circumference and a circular lower peripheral edge with a second circumference that is larger than the first circumference, the circular lower peripheral edge having one to eight indentations. In some embodiments, the upper peripheral edge of the frustoconical ring has an inner circumference that substantially coincides with the corneal limbus. In some embodiments, the curved lateral portion of the frustoconical ring has a pitch that is at least about 4 millimeters. In some embodiments, the exterior surface of the curved lateral portion includes at least one demarcation adjacent to at least one indentation indicating a position corresponding to about 3.5 millimeter from the upper edge. In some embodiments, the demarcation is placed adjacent to each indentation. In some embodiments, the curved lateral portion of the incurvate body has a roughened underside. In some embodiments, the lower peripheral edge of the frustoconical ring includes four indentations, the first and second indentations being about 50° apart, the second and third indentations being about 130° apart, the third and fourth indentations being about 50° apart, and the fourth and first indentations being about 130° apart.

In some embodiments, the positioning device includes two mounting members disposed on the upper peripheral edge of the frustoconical ring at opposing positions, one of which is about equal distance from the second and third indentations on the upper peripheral edge and the other is about equal distance from the fourth and first indentations on the upper peripheral edge.

In some embodiments, the positioning device includes a handle, one end of which has a two-prong portion, each prong being pivotably attached to a mounting member on the frustoconical ring. In some embodiments, each prong is attached to a mounting member using a pin inserted through openings on the prong and mounting member, through ball-and-socket joint or through a cylindrical-type snap fit joint.

In some embodiments, the lower peripheral edge of the frustoconical ring includes eight indentations about 45° apart.

In some embodiments, the upper peripheral edge of the frustoconical ring has an inner circumference that is larger than the circumference of the corneal limbus.

In some embodiments, the indentations on the lower peripheral edge are U-shaped.

In some embodiments, the indentations are effective to receive a surgical instrument including a trocar, infusion cannula, blade, needle, cotton-tipped applicator, fluid line, fiberoptic light source, light or laser probe, torpedo light, aspirator, extendable pic, vertical curved scissors, membrane brush or vitrectomy probe.

In some embodiments, the positioning device is made of material that includes metal, plastic or any combination thereof. In some embodiments, the positioning device is made of material that includes martensitic steel. In some embodiments, the positioning device is made of material that includes chromium, nickel, molybdenum, carbon, manganese, titanium, acetal copolymer, high-density polyethylene, nylon, polycarbonate, polyethermide, polyphenyl sulfone, polypropylene, acrylonitrile butadiene styrene, acrylic or any combination thereof.

In another aspect, the invention provides a positioning device having an incurvate body that is a semi-circular segment of a frustoconical ring, the segment having one to eight indentations on its lower peripheral edge. In some embodiments, the lower peripheral edge of the incurvate body has four indentations, the second and third indentations being about 50° apart, and each of the first and fourth indentations being about 32° to about 33° relative to the nearest terminal edge of the incurvate body. In some embodiments, the upper peripheral edge of the incurvate body substantially aligns with a portion of the corneal limbus. In some embodiments, the pitch of the incurvate body is about 4 millimeters. In some embodiments, the exterior surface of the curved lateral portion of the incurvate body includes at least one demarcation adjacent to at least one indentation indicating a position corresponding to about 3.5 millimeter from the upper peripheral edge. In some embodiments, the demarcation is placed adjacent to each indentation. In some embodiments, the curved lateral portion has a roughened underside. In some embodiments, the lower peripheral edge of the incurvate body has four indentations, the second and third indentations being about 50° apart and each of the first and fourth indentations being about 32° to about 33° relative to the nearest terminal edge. In some embodiments, the indentations on the lower peripheral edge are U-shaped. In some embodiments, a mounting member is disposed on the upper peripheral edge of the incurvate body at equal distance between the second and third indentations. In some embodiments, the positioning device also includes a handle, one end portion of which is pivotably attached to the mounting member on the incurvate body. In some embodiments, the end portion is attached to the mounting member using a pin inserted through openings on the end portion of the handle and on the mounting member, through ball-and-socket joint or through a cylindrical-type snap fit joint. In some embodiments, the positioning device is made of material that includes metal, plastic or any combination thereof. In some embodiments, the positioning device is made of material that includes martensitic steel. In some embodiments, the positioning device is made of material that includes chromium, nickel, molybdenum, carbon, manganese, titanium, acetal copolymer, high-density polyethylene, nylon, polycarbonate, polyethermide, polyphenyl sulfone, polypropylene, acrylonitrile butadiene styrene, acrylic or any combination thereof.

Thus, in some embodiments, the positioning device is used for eye fixation and stabilization, as well as to assist in accurate instrument positioning, introduction and/or manipulation during eye examinations, surgeries or procedures. In some embodiments, the positioning device can be used in anterior segment surgery such as, for example, cataract surgery and refractive surgery, as well as for vitreoretinal procedures and posterior segment surgeries such as, for example, virectomy and intravitreal injections.

Any feature or combination of features described herein are included within the scope of the present invention provided that the features included in any such combination are not mutually inconsistent as will be apparent from the context, this specification and the knowledge of one of ordinary skill in the art.

Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are illustrative only and not intended to be limiting. Although methods and materials similar or equivalent to those described herein can be used to practice the invention, suitable methods and materials are described below.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Other features and advantages of the invention will be apparent from the following detailed description and from the claims.

DETAILED DESCRIPTION

The invention provides a positioning device that can be used in an eye examination, eye surgery or other eye procedures. A positioning device of the invention includes an upper peripheral edge with a first arc length, a lower peripheral edge with a second arc length longer than the first arc length, and a curved lateral wall therebetween, the positioning device having one to eight indentations on its lower peripheral edge. The upper peripheral edge, curved lateral wall and lower peripheral edge are configured to engage at least a portion of the eye that is posterior to the corneal limbus beneath which the pars plana is located. The positioning device can include a handle pivotably attached to the upper peripheral edge for ease of use.

Illustrative Embodiment

Figure 1:
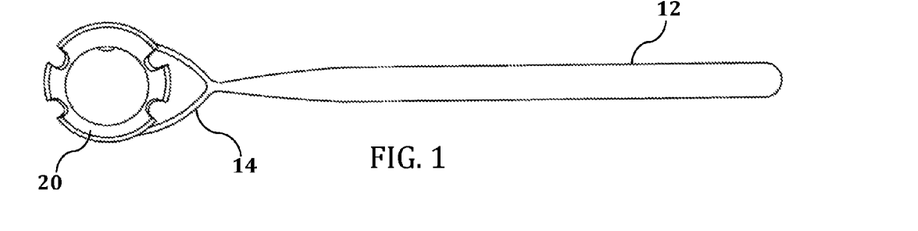
FIG. 1 is positioning device 10 with handle 12 terminating in two-prong terminus 14 attached to frustoconical ring 20, as viewed from the underside of the frustoconical ring 20.

A specific embodiment of a positioning device of the invention is illustrated in FIG. 1. Positioning device 1 has handle 10 pivotably attached to an incurvate body with the structure of frustoconical ring 20. Handle 10 includes elongated shaft 12 with two-prong terminus 14, through which handle 10 is pivotably joined to frustoconical ring 20.

Figure 2:
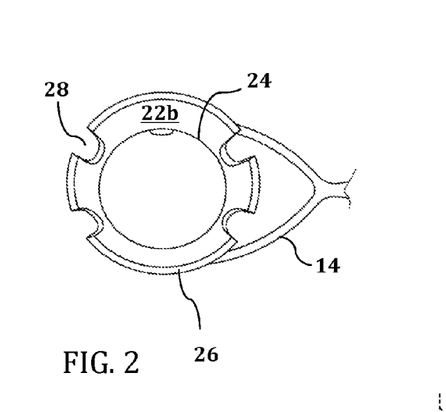
FIG. 2 is an enlarged view of one end of positioning device 10 with frustoconical, ring 20 as seen from its underside.
Figure 3:
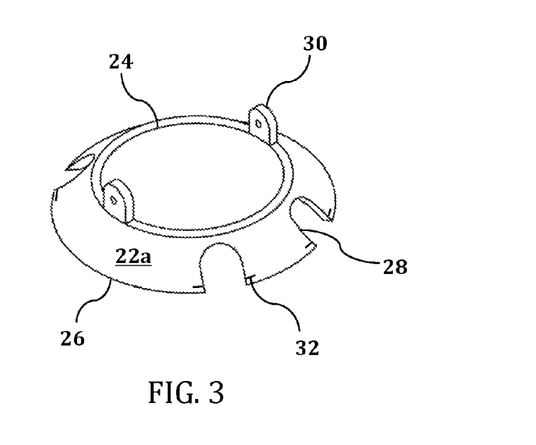
FIG. 3 is a perspective view of frustoconical ring 20 with upper peripheral edge 24, curved lateral portion 22 extending to lower peripheral edge 26, indentation 28 with demarcation 32, and mounting wing 30.
Figure 4:
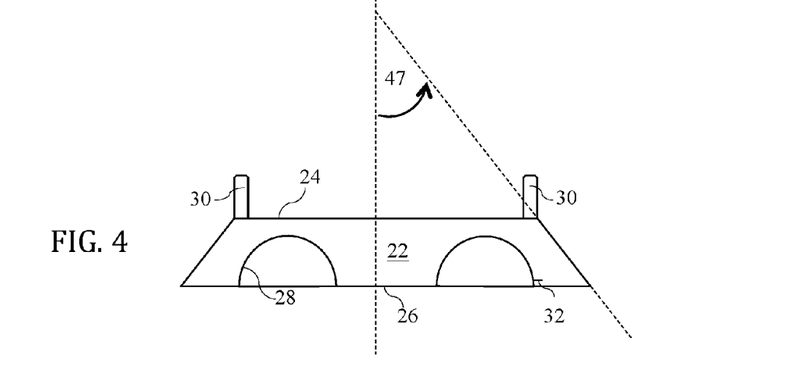
FIG. 4 is a side view of frustoconical ring 20 showing that curved lateral portion 22 is about 47° with respect to the central axis of rotation.
Figure 5:
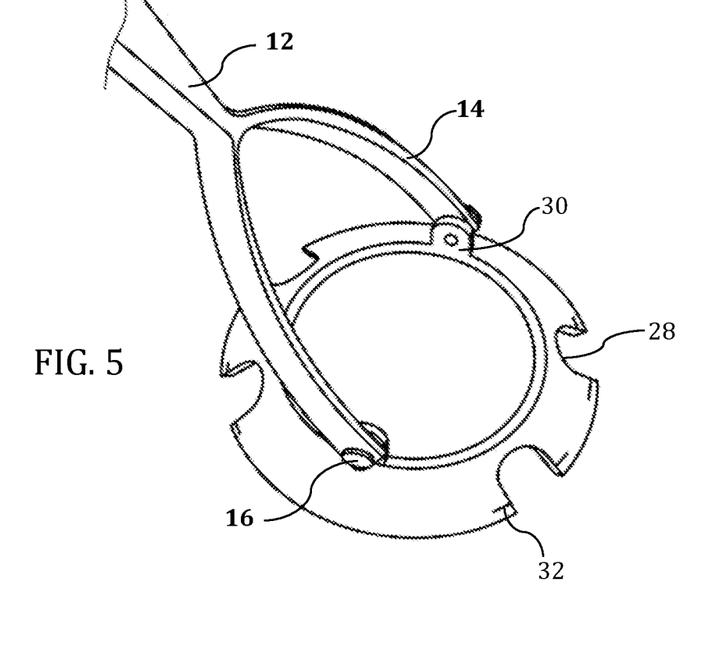
FIG. 5 is an enlarged view of one end of positioning device 10 showing that two-prong terminus 14 is pivotably joined to frustoconical ring 20 at mounting wing 30 using pin 16.

FIGS. 2-5 illustrate the structure of frustoconical ring 20, which has curved lateral portion 22, upper peripheral edge 24 and lower peripheral edge 26 with four of indentation 28 (FIGS. 2-4). Upper peripheral edge 24 defines an opening having a diameter about commensurate with the cornea (FIG. 7), so that when placed on the eye, the inner circumference of upper peripheral edge 24 coincides approximately with the corneal limbus. Curved lateral portion 22 extends about 4 millimeters from upper peripheral edge 24, radially and at an angle of taper of about 47° with respect to the central axis about which frustoconical ring 20 has a rotational symmetry (FIG. 4). The four of indentation 28, each of which sized to receive a surgical instrument, e.g. about 2.8 millimeters wide, are spaced in a symmetrical pattern on frustoconical ring 20 (FIGS. 2, 5). Positioning device 1 also includes demarcation 32 adjacent to indentation 28 marking a position that is about 3.5 millimeters from the corneal limbus (FIGS. 3, 5).

Figure 6:
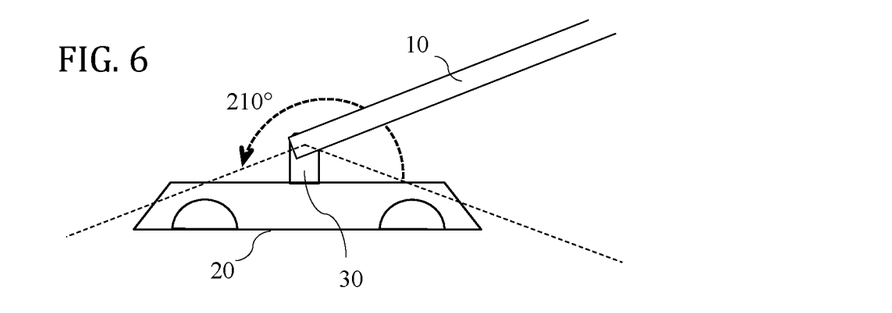
FIG. 6 is a side view of positioning device 10 showing the range of rotation of handle 10 on mounting wing 30 with respect to frustoconical ring 20.

Frustoconical ring 20 includes two of mounting wing 30 for pivotably attaching handle 10 (FIGS. 4 & 5). Handle 10 includes elongated shaft 12 with two-prong terminus 14, each prong being pivotably mounted onto wing 30 using pin 16, which is inserted through an opening at the end portion of each prong and through an opening on each of wing 30 (FIG. 5). Configured as such, handle 10 has an angle of pivot or swivel of about 210° (FIG. 6) and can be tilted as needed with respect to frustoconical ring 20 for maximum flexibility and usability.

Components of positioning device 1 are summarized below.

| COMPONENTS | REF. NO. | COMPONENT | REF. NO. |
| --- | --- | --- | --- |
| Handle | 10 | Frustoconical ring | 20 |
| Elongated shaft | 12 | Curved lateral portion | 22 |
| Two-prong terminus | 14 | Upper peripheral edge | 22 |
| Demarcation | 32 | Lower peripheral edge | 24 |
|  |  | Indentation | 28 |
|  |  | Mounting member | 30 |

Incurvate Body

The incurvate body can be a frustoconical ring as exemplified above in positioning device 1. As used herein, the term "frustoconical" refers to the structure formed by the lateral surface of a frustum or truncated cone (in particular, a right circular cone) in which the plane cutting off the apex is parallel to the base of the cone. A frustum or truncated cone, as illustrated in FIG. 7, has smaller upper base with a circular, upper peripheral edge, a larger lower base with a circular, lower peripheral edge, and a lateral surface therebetween.

Figures 7, 8A:
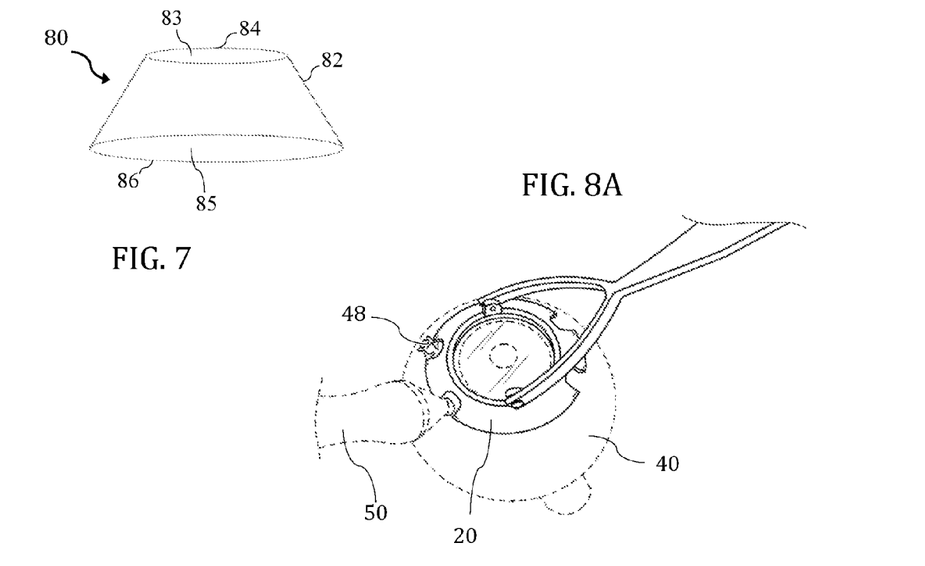
FIG. 7 is an illustration of the upper peripheral edge, lower peripheral edge and lateral surface of a frustoconical ring.
FIGS. 8A-8C are illustrations of the relative positions of a frustoconical ring of the invention with respect to the corneal limbus and the portion of the eye that is posterior to the corneal limbus beneath which the pars plana is located.

Frustum 80, for example, has lateral surface 82 disposed between smaller upper base 83 with circumference 84 and larger lower base 85 with larger circumference 86 (FIG. 7).

Similarly, an incurvate body of the invention such as frustoconical ring 20 (FIG. 2, 3) has curved lateral portion 22 (with external surface 22a and an inner or underside surface 22b) disposed between circular, upper peripheral edge 24 and circular, lower peripheral edge 26. Upper peripheral edge 24 defines a circular opening that expands to its widest at lower peripheral edge 26, and the distance between the upper peripheral edge and the lower peripheral edge being the pitch of the frustoconical ring. Thus, as used herein, the pitch of an incurvate body refers to the distance between the upper peripheral edge and the lower peripheral edge of the curved lateral portion.

The curved lateral portion of the incurvate body or frustoconical ring has an inner or underside surface 22b and an exterior surface 22a that are generally parallel, though the inner or underside surface 22b can be roughened by mechanical grinding or polishing, using a grit abrasive, or by electropolish to improve traction with the eye and facilitate grip as needed. As such, the curved lateral portion 22 is generally of uniform thickness overall. The term "thickness," as used herein in reference to the curved lateral portion of an incurvate body or frustoconical ring, refers to the distance between the exterior surface and inner or underside surface of the curved lateral portion. The thickness of the curved lateral portion can be about 0.2 millimeter to about 1.5 millimeters thick, for example, about 0.3, about 0.5, about 0.7, about 0.9, about 1.1, about 1.3, or about 1.5 millimeters thick.

The curved lateral portion of an incurvate body or frustoconical ring has a fixed angle of taper as illustrated in FIG. 4. The angle of taper can be between about 40° to about 55°, for example, about 43°, about 45°, about 47°, about 49° about 51°, or about 53° relative to the central axis of rotation. Thus, the angle between opposing points on the inner lateral surface or across the inner diameter of the incurvate body or frustoconical ring can be about 88° to about 100°, for example, about 90°, about 92°, about 94°, about 96° or about 98°. The inner surface of the curved lateral portion can have any angle of taper that is substantially congruous with the contour of at least a portion of the eye beneath which the pars planar is located so as to engage and limit movement of the eye. That is, the angle of taper conforms to the contours of the eye so as to facilitate engagement with the eye during use. To further improve fraction, the inner surface of the curved lateral portion can be subjected to mechanical grinding, mechanical polishing, roughening using a grit abrasive, or electropolishing to increase surface roughness as needed to improve grip.

Figure 8B:
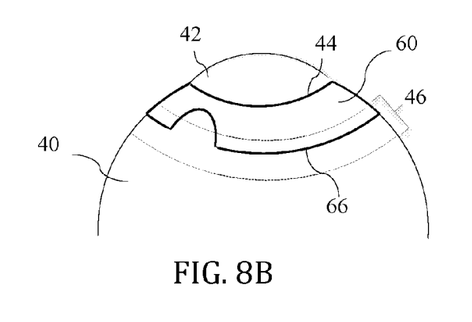
Figure 8C:
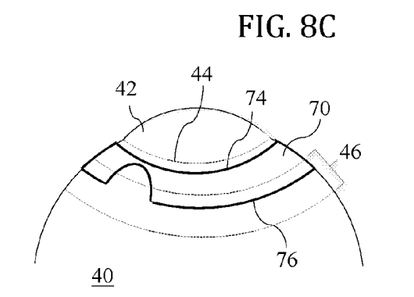

The incurvate body or frustoconical ring is configured to engage at least a portion of the eye posterior to the corneal limbus and beneath which the pars plana is located. FIGS. 8A-8C illustrates the position of the incurvate body or frustoconical ring relative to the cornea when a positioning device of the invention is placed on the eye. Eye globe 40 includes cornea 42, corneal limbus 44, and region 46, the approximate region of the eye surface beneath which the pars plana is located, and generally known to those of skill in the art as being about 3 millimeters to about 6 millimeters from the corneal limbus.

Components discussed in FIGS. 7-8 are summarized below.

| COMPONENTS | REF. NO. | COMPONENT | REF. NO. |
|---|---|---|---|
| Frustum | 80 | | |
| Lateral wall | 82 | Upper base | 83 |
| Upper peripheral edge | 84 | Lower base | 85 |
| Lower peripheral edge | 84 | | |
| Eye globe | 40 | Frustoconical ring | 60 |
| Cornea | 42 | Upper peripheral edge | 64 |
| Corneal limbus | 44 | Lower peripheral edge | 66 |
| Pars plana region | 46 | Frustoconical ring | 70 |
| Trocar cannula | 48 | Upper peripheral edge | 74 |
| Trocar system | 50 | Lower peripheral edge | 76 |

The incurvate body or frustoconical ring engages with at least a portion of region 46. The incurvate body or frustoconical ring can engage with the portion of region 46 most proximate to the cornea as illustrated in FIGS. 8A and 8B, the portion of region 46 most distal to the cornea, the center portion of region 46, or a combination thereof. Accordingly, the incurvate body or frustoconical ring can engage with about one-third or more of region 46, for example half, two thirds or all of region 46.

In some embodiments, the upper peripheral edge of the incurvate body or frustoconical ring has an inner circumference that approximates the circumference of the cornea. As such, the inner circumference can be coextensive or coincides with the corneal limbus when the positioning device is placed on the eye (FIGS. 8A & 8B). The diameter of the opening defined by the upper peripheral edge can be about 11.5 millimeters, about 12 millimeters, or about 12.5 millimeters. In FIG. 8B, the upper peripheral edge of frustoconical ring 60 has an inner circumference that coincides with the location of corneal limbus 44. In these embodiments, the pitch of the incurvate or frustoconical ring, i.e. the distance between the upper peripheral edge and the nearest point on the lower peripheral edge, can be, for example, about 4, about 4.5, about 5, about 5.5 or about 6 millimeters.

Alternatively, the upper peripheral edge can have an inner circumference larger than the circumference of the cornea. For example, frustoconical ring 70 illustrated in FIG. 8C has upper peripheral edge 74 that does not coincide with corneal limbus 44, but is posterior to corneal limbus 44. Upper peripheral edge 74 defines an opening having a diameter larger than the diameter of cornea 42. Where the upper peripheral edge has a circumference larger than the circumference of the cornea, the circumference of the upper peripheral edge can be, for example, about 0.5, about 1, about 1.5, about 2, about 2.5, about 3, about 3.5 or about 4 millimeters posterior to the corneal limbus.

In some embodiments, the incurvate body can be a segment of any frustoconical ring structure described above. As such, the incurvate body can have the structure of an arc of any arc length that is less than a full circle, that is, an arc that extends less than 360°, for example and without limitation, an arc that extends about 270°, about 200°, about 180° or about 120°, so long as the frustoconical ring segment has the thickness, pitch and curvature substantially as described above for the frustoconical ring. FIGS. 9C and 9D illustrate the structure of various embodiments of an incurvate body of the invention having a segmented ring structure.

Mounting Member

The incurvate body can optionally have one or two mounting members disposed on the upper peripheral edge of the incurvate body for pivotably attaching a handle to the incurvate body.

Figure 10A:
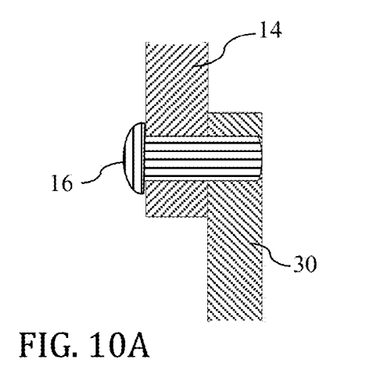
FIGS. 10A-10D are cross-sectional or side views of various handle termini and mounting means that can mate to form a swivel joint between a handle and an incurvate body of the invention to allow the handle to be pivotably attached to the incurvate body
Figure 10B:
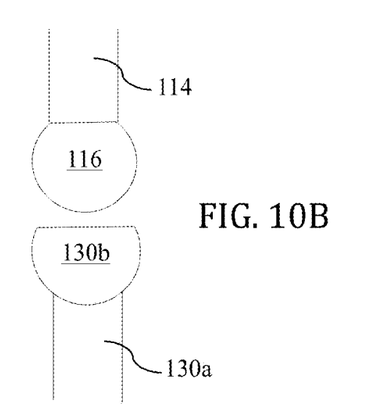
Figure 10C:
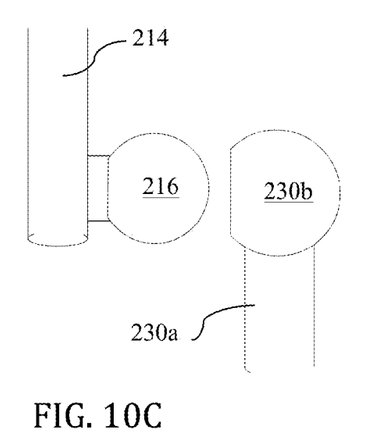
Figure 10D:
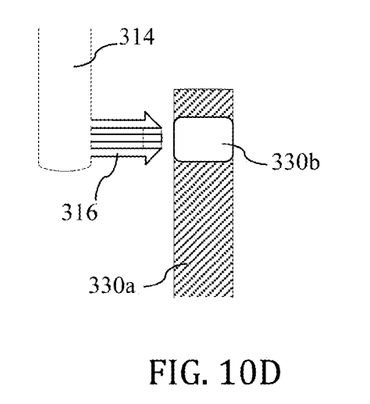

The mounting member can have any structure to which the handle can be pivotably attached that is known to those of skill in the art. For example, the mounting members can be a mounting wing having a flat structure with an opening configure to accommodate a pin or cylindrical-type snap fit member such as shown in FIGS. 3-5, 7, 10A, 10C and 10D. Alternatively, the mounting member can include a socket effective to mate with a spherical knob on the end of the handle to form a ball and socket joint as shown in FIGS. 11B and 10C. In FIG. 10A, a vertical cross-sectional view of a prong of the two-prong terminus 14, pin 16 and mounting wing 30 (shown in FIG. 5) is provided. In FIG. 10D, a vertical cross-sectional view of mounting wing 330 is provided to illustrate opening 330b and the cylindrical-type snap-fit mechanism that can be used in a device of the invention. Thus, any mechanisms known to those of skill in the art can be used to pivotably attach the handle to the incurvate body including, for example, a clevis pin, a cotter pin, or a self-locking pin; or a ball-and-socket and/or a snapfit mechanism such as for example, a cantilever beam, cylindrical-type or spherical-type snap fit as further described below and illustrated herein.

In embodiments having two mounting members, the mounting members can be disposed in opposing positions on the upper peripheral edge of an incurvate body as illustrated in FIGS. 3 and 5. As such, the mounting members can be about 180° apart. In these embodiments, a handle having a two-prong terminus as illustrated in FIG. 5 can be used. In these embodiments, each prong of the two-prong handle terminus is pivotably attached to each mounting member using any mechanisms known to those of skill in the art as discussed above.

Indentations & Demarcations

The incurvate body can have one to eight indentations as illustrated in FIGS. 1-5 and FIGS. 9A-9D. The indentations can be in a symmetrical or asymmetrical pattern, as well as at equidistance apart along the lower peripheral edge or otherwise.

Figure 9A:
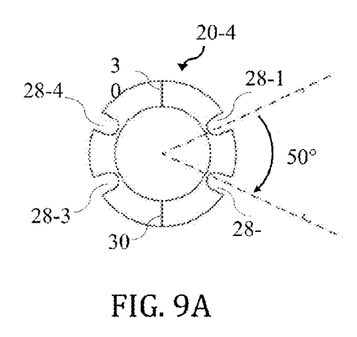
FIGS. 9A-9D are various embodiments of an incurvate body of the invention and the possible position(s) of the one to eight indentation(s) at the lower peripheral edge of the incurvate body.

FIG. 9A illustrates an embodiment of the invention in which the incurvate body is a frustoconical ring having four indentations at the lower peripheral edge. In this embodiment, four indentations can be positioned as shown in which two indentations are about 50° apart at position 28-1 and 28-2 on one side, and the other two indentations are also positioned about 50° apart on the opposing side at position 28-3 and 28-4. Arranged as such, position 28-1 is about 130° from position 28-4, and similarly, position 28-2 is about 130° from position 28-3. Where the incurvate body includes two optional mounting member 30, each indentation can be about 65° from the nearest mounting member 30. FIG. 9A illustrates the relative positions of one to four indentations in some embodiments of the invention. Thus, where a incurvate body of the invention has a frustoconical ring structure, the incurvate body can have (1) an indentation at any of the four positions illustrated in FIG. 9A, (2) two or three indentations at any combination of the four possible positions illustrated in FIG. 9A, or (3) four indentations at all positions illustrated in FIG. 9A.

Figure 9B:
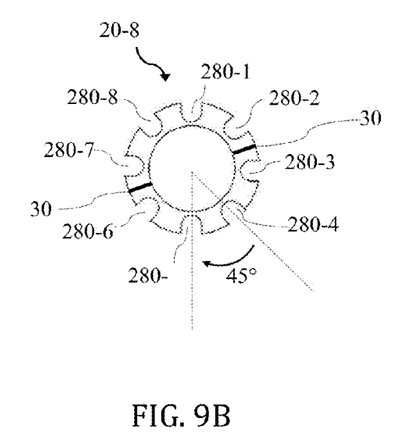
Figure 9C:
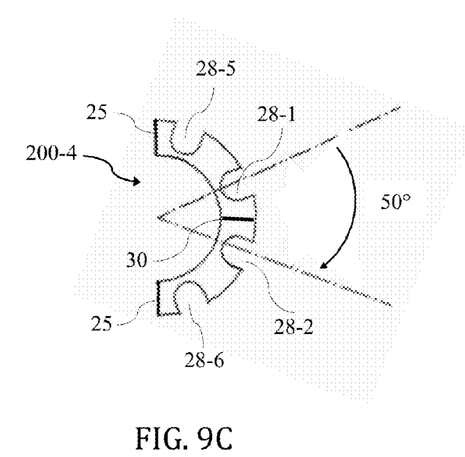
Figure 9D:
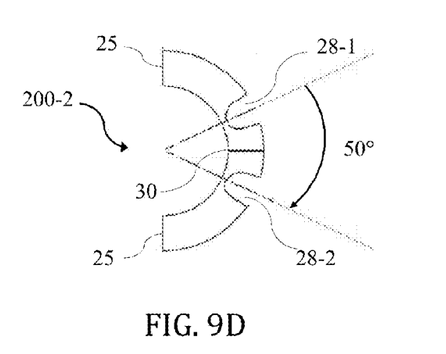

FIG. 9B illustrates an embodiment of the invention in which the incurvate body is a frustoconical ring having eight indentations at the lower peripheral edge. In this embodiment, the eight indentations can be evenly positioned about 45° apart at positions 280-1 to 280-8 along the lower peripheral edge. Where the incurvate body includes two optional mounting member 300, the mounting member 300 can be positioned on the upper peripheral edge at equidistance between any two indentations. FIG. 9B illustrates the relative positions of one to eight indentations in some embodiments of the invention. Where a incurvate body of the invention has a frustoconical ring structure, the incurvate body can have (1) an indentation at any of the eight positions illustrated in FIG. 9B, (2) two to seven indentations at any combination of the eight possible positions illustrated in FIG. 9B, or (3) eight indentations at all positions illustrated in FIG. 9B.

In other embodiments where the incurvate body is a frustoconical ring, three indentations can be about 120° apart and four indentations can be about 90° apart on the lower peripheral edge. In these embodiments, where there are two or three indentations on the lower peripheral edge, the indentations can be about 120°, about 90° or about 45° apart.

FIG. 9C illustrates an embodiment of the invention in which the incurvate body is a frustoconical ring segment of about 180° arc that has four indentations at its lower peripheral edge. In this embodiment, two of the four indentations can be about 50° apart at about 65° and about 115° relative to terminal edge 25, i.e. position 28-1 and 28-2, respectively, while the remaining two indentations can be about 32° to about 33° relative to terminal edge 25, i.e. position 28-5 and 28-6. Alternatively, all four indentations can be about 45° apart as analogous to the positions illustrated in FIG. 9B, in which case the first and last indentation can be about 22.5° from the nearest terminal edge of the incurvate body (while the remaining two indentations can be about 67.5° and about 112.5° from a terminal edge 25). Where the incurvate body includes an optional mounting member 30, mounting member 30 can be positioned on the upper peripheral edge equidistance between position 28-1 and 28-2. Alternatively, two mounting members can be position near the terminal edges of the incurvate body. FIG. 9C illustrates the relative positions of one to four indentations in embodiments of the invention in which the incurvate body is a semi-circular, frustoconical ring segment. In these embodiments, the incurvate body can have (1) an indentation at any of the four positions illustrated in FIG. 9C, i.e. position 28-1, 28-2, 28-5 and 28-6; (2) two or three indentations at any combination of these four possible positions; or (3) four indentations at all four of these positions. For example, two indentations can be disposed 50° apart at position 28-1 and 28-2 on either side of optional mounting member 30 as shown in FIG. 9D.

In other embodiments where the incurvate body is a frustoconical ring segment, for example, one of about 180° arc, eight indentations can be about 20° apart, four indentations can be about 36° apart, and three indentations can be about 45° apart on the lower peripheral edge. Thus, where there are two or three indentations on the lower peripheral edge, the indentations can be about 20°, about 36°, or about 45° apart.

Components discussed in FIG. 9 are summarized below.

| COMPONENTS | REF. NO. | COMPONENT | REF. NO. |
|---|---|---|---|
| Frustoconical ring | 20-4 | Frustoconical ring segment | 200-4 |
| Optional mounting member | 30 | Optional mounting member | 30 |
| Indentation position | 28-1 | Indentation position | 28-1 |
| Indentation position | 28-2 | Indentation position | 28-2 |
| Indentation position | 28-3 | Indentation position | 28-5 |
| Indentation position | 28-4 | Indentation position | 28-6 |
|  |  | Terminal edge | 25 |
| Frustoconical ring | 20-8 |  |  |
| Optional mounting member | 30 |  |  |
| Indentation position | 280-1 | Indentation position | 280-5 |
| Indentation position | 280-2 | Indentation position | 280-6 |
| Indentation position | 280-3 | Indentation position | 280-7 |
| Indentation position | 280-4 | Indentation position | 280-8 |
| Frustoconical ring segment | 200-2 |  |  |
| Terminal edge | 25 | Indentation position | 280-1 |
| Optional mounting member | 30 | Indentation position | 280-2 |

The indentations can have any shape including V- or U-shapes. The indentation can be of a size sufficient to receive a surgical instrument that contacts the sclera during an eye examination, procedure or surgery as illustrated in FIG. 8A for trocar cannula 48 or trocar system 50. Thus, the indentation can be of a size sufficient to receive, for example, a trocar, infusion cannula, blade, needle, cotton-tipped applicator, fluid line, fiberoptic light source, light or laser probe, torpedo light, aspirator, extendable pic, vertical curved scissors, membrane brush, fragmatome and vitrectomy probe. The indentation can have an arc of, for example, about 2 to about 4 millimeters, for example, about 2.2, about 2.4, about 2.6, about 2.8, about 3, about 3.2, about 3.4 or about 3.6 millimeters.

The external surface of the curved lateral portion of the incurvate body can have one or more demarcations adjacent to the one or more indentations indicating one or more distances posterior to the corneal limbus, including, for example, a distance of about 1 millimeter, about 1.5 millimeters, about 2 millimeters, about 2.5 millimeters, about 5 millimeters, about 3.5 millimeters, or any combination thereof.

Handle

The device of the invention can optionally include a handle to assist in placement of the incurvate body on the eye. The handle can be pivotably attached to the incurvate body for flexibility in positioning the handle, as well as improved handling and manipulation of the device during use. The handle can include an elongated shaft having a first end portion configured to pivotably attach to the incurvate body through an optional mounting member on the upper peripheral edge of the incurvate body. The first end portion can include a two-prong terminus, each prong being configured to pivotably attach to a mounting member on the upper peripheral edge of the incurvate body using any means known to those of skill in the art. The first end portion or each prong can be a flat structure with an opening for insertion of a pin as shown in FIG. 10A. The first end portion or each prong on a two-prong terminus can include a spherical knob effective to mate with a socket on the mounting member as shown in FIG. 10B or 10C to form a ball-and-socket link with the incurvate body. The first end portion or each prong on a two-prong terminus can include a cylindrical-type snap-fit for matting with a cylindrical opening in the mounting member as illustrated in FIG. 10D.

Components discussed in FIGS. 10A-10D are summarized below.

| COMPONENTS | REF. NO. | COMPONENT | REF. NO. |
|---|---|---|---|
| Pin | 16 | Handle end | 214 |
| Handle prong | 14 | Spherical knob | 216 |
| Mounting wing | 30 | Mounting socket | 230b |
|  |  | Mounting member | 230a |
| Handle end | 14 |  |  |
| Spherical knob | 116 | Handle end | 314 |
| Socket of mounting member | 130b | Cylinder-type snap-fit | 316 |
| Mounting member | 130a | Mounting member | 330a |
|  |  | Mounting member opening | 330b |

Positioning Device of the Invention

A positioning device of the invention can be constructed as a reusable device that can be sterilized as is typical for a surgical instrument or constructed as a single-use or disposable device. A positioning device of the invention also can be constructed with a combination of reusable and single-use parts. For example, the incurvate body can be constructed for single-use to be paired with a reusable handle.

A positioning device of the invention can be constructed of any materials known to those of skill in the art including a variety of metals or metal alloys including stainless steel, one or more synthetic polymers or any combination thereof. A positioning device can be constructed of various types of stainless steel (e.g. dumoxel, austenite, martensitic, ferritic, precipitation-hardening martensitic, duplex, surgical stainless steel), titanium, tungsten carbide, dumostar (steel, chromium, nickel and cobalt) or any combination thereof. Thus, a positioning device of the invention can be made of iron, chromium, carbon, nickel, silicon, manganese, phosphorus, sulphur, aluminum, titanium, molybdenumchrome or any combination thereof. A positioning device of the invention can be made of plastics including acetal copolymer, high-density polyethylene, nylon, polycarbonate, polyethermide, polyphenylsulfone, polypropylene, acrylonitrile butadiene styrene, acrylic or any combination thereof.

Any materials and methods known to those of skill in the art for constructing medical instruments can be used to manufacture a positioning device of the invention. See, for example, Randy Pell, *Surgical Instruments: Converting from Metal to Plastic*, in Medical Device & Diagnostic Industry, October 2006, Canon Communications, LLC 2006, available at mack.com/resource/MDDI_Oct06_RPell.pdf (last retrieved Aug. 10, 2013). See also Helmut Kapczynski, *Surgical Instruments 101—An Introduction to KMedic Certified Instruments*, 1997, available at teleflex.com/en/usa/pdf/KMedic_Surgical_Instruments_101.pdf (last retrieved Aug. 10, 2013); Surgical Stainless steel, available at en.wikipedia.org/wiki/Surgical_stainless_steel (last visited Aug. 13, 2013); and martensite, available at en.wikipedia.org/wiki/Martensite (last visited Aug. 13, 2013). A positioning device of the invention can be made using any means known to those of skill in the art including by injection molding. The surface finish on the underside of the incurvate body can be modified as needed to improve traction with the eye using any method known to those of skill in the art including by mechanical grinding, mechanical polishing or electropolish. A grit abrasive such as aluminum oxide or silicon carbide sandpaper of, for example, 80 to 100 grit, 120 grit, 150 grit, 180 grit, can be used to achieve a select roughness. The desired surface roughness can also be achieved by electropolish to a range from 150 grit finish to 320 grit finish.

A positioning device of the invention can be used to position and stabilize the eye during various procedures, surgeries and examinations, as well as to enable accurate positioning and manipulation of instruments. A positioning device can be used for procedure or surgery involving the anterior or posterior segment of the eye including stabilization for cataract, LASIK and other refractive eye surgeries, anterior segment taps, intravitreal injections, for example, of anti-VEGF, steroid, antibiotic or any pharmaceutical to be injected intravitreally, and for vitreoretinal surgery, in particular, small gauge vitreoretinal surgery or trans pars plana vitrectomy. A positioning device of the invention can be used during the preliminary steps of introducing and placement of surgical instruments such as trocars, illumination instruments and the like, then removed from the eye once the select instruments are in place. Alternatively, a positioning device of the invention can be left on the eye for the duration of the procedure.

The specific embodiments of the invention described above do not limit the scope of the invention described in the claims.

OTHER EMBODIMENTS OF THE INVENTION

While the invention has been described in conjunction with the detailed description, the foregoing description is intended to illustrate and not limit the scope of the invention, which is defined by the scope of the appended claims. Other aspects, advantages, and modifications are within the scope of the following claims.

The specific methods and devices described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Under no circumstances may the patent application be interpreted to be limited to the specific examples or embodiments or methods specifically disclosed herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as described in the statements of the invention and as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. In addition, the invention has been described broadly and generically herein. Each of the narrower species and subgeneric groupings falling within the generic disclosure also form part of the invention.

What is claimed is:

1. A positioning device for use in an eye procedure comprising an incurvate body that comprises a frustoconical ring structure configured to engage at least a portion of the eye posterior to the corneal limbus and beneath which the pars plana is located, the incurvate body comprising:
   (a) an upper peripheral edge having a first arc length, the upper peripheral edge configured to substantially coincide with the corneal limbus when the device is placed on the eye,
   (b) a lower peripheral edge having a second arc length that is longer than the first arc length, the lower peripheral edge comprising four indentations of a size effective to receive an infusion cannula, the first and second indentations being about 50° apart, the second and third indentations being about 130° apart, the third and fourth indentations being about 50° apart, and the fourth and first indentations being about 130° apart,
   (c) a curved lateral portion extending between the upper and lower peripheral edges, and
   (d) two mounting members disposed on the upper peripheral edge at opposing positions, one of which is about equal distance from the second and third indentations and the other is about equal distance from the fourth and first indentations.

2. The positioning device of claim 1, further comprising a handle, one end of which comprises a two-prong portion, each prong being pivotably attached to one of the mounting members.

3. The positioning device of claim 2, wherein each prong is attached to one of the mounting members using a pin inserted through openings on the prong and the respective mounting member, through ball-and-socket joint or through a cylindrical-type snap fit joint.

4. The positioning device of claim 1, wherein the curved lateral portion comprises an exterior surface on which at least one demarcation is disposed adjacent to at least one indentation of the four indentations, the demarcation indicating a position about 3.5 millimeter from the corneal limbus when the device is placed on the eye.

5. The positioning device of claim 4, wherein a demarcation is disposed on the exterior surface of the curved lateral portion adjacent to each indentation of the four indentations.

6. The positioning device of claim 1, wherein the curved lateral portion comprises a roughened underside.

7. A positioning device for use in an eye procedure comprising an incurvate body with a frustoconical ring structure configured to engage at least a portion of the eye posterior to the conical limbus and beneath which the pars plana is located, the incurvate body comprising:
   (a) an upper peripheral edge having a first arc length and an inner circumference configured to be larger than the circumference of the corneal limbus when the device is placed on the eye,
   (b) a lower peripheral edge having a second arc length that is longer than the first arc length, the lower peripheral edge comprising one to eight indentations of a size effective to receive a surgical instrument,
   (c) a curved lateral portion extending therebetween having an exterior surface on which at least one demarcation is disposed adjacent to at least one indentation of the one to eight indentations, the demarcation indicating a position about 3.5 millimeter from the corneal limbus when the device is placed on the eye,
   (d) two mounting members disposed at opposing positions on the upper peripheral edge, and
   (e) a handle, one end of which comprises a two-prong portion, each prong being pivotally attached to one of the mounting members.

8. The positioning device of claim 7, wherein each prong is attached to one of the mounting members using a pin inserted through openings on the prong and the respective mounting member, through ball-and-socket joint or through a cylindrical-type snap fit joint.

9. The positioning device of claim 7, wherein the curved lateral portion comprises an angle of about 40° to about 55° relative to a line normal to a plane parallel to the upper and lower peripheral edges.

10. The positioning device of claim 7, wherein a demarcation is disposed on the exterior surface of the curved lateral portion adjacent to each indentation of the one to eight indentations.

11. The positioning device of claim 7, wherein the curved lateral portion comprises a roughened underside.

12. The positioning device of claim 7, wherein the lower peripheral edge comprises eight indentations about 45° apart.

13. The positioning device of claim 7, which comprises martensitir steel, chromium, nickel, molybdenum, carbon, manganese, titanium, acetal copolymer, high-density polyethylene, nylon, polycarbonate, polyethermide, polyphenyl sulfone, polypropylene, acrylonitrile butadiene styrene, acrylic or any combination thereof.

14. A positioning device for use in an eye procedure comprising an incurvate body that comprises a frustoconical ring structure configured to engage at least a portion of the eye posterior to the corneal limbus and beneath which the pars plana is located, the incurvate body comprising:
   (a) an upper peripheral edge having a first arc length, the upper peripheral edge configured to substantially coincide with the corneal limbus when the device is placed on the eye,
   (b) a lower peripheral edge having a second arc length that is longer than the first arc length, the lower peripheral edge comprising four indentations of a size effective to receive a surgical instrument, the first and second indentations being about 50° apart, the second and third indentations being about 130° apart, the third and fourth indentations being about 50° apart, and the fourth and first indentations being about 130° apart,
   (c) a curved lateral portion extending between the upper and lower peripheral edges, and
   (d) two mounting members disposed on the upper peripheral edge at opposing positions, one of which is about equal distance from the second and third indentations and the other is about equal distance from the fourth and first indentations.

15. The positioning device of claim 14, further comprising a handle, one end of which comprises a two-prong portion, each prong being pivotably attached to one of the mounting members.

16. The positioning device of claim 15, wherein each prong is attached to one of the mounting members using a pin inserted through openings on the prong and the respective mounting member, through ball-and-socket joint or through a cylindrical-type snap fit joint.

17. The positioning device of claim 14, wherein the curved lateral portion comprises an exterior surface on which at least one demarcation is disposed adjacent to at least one indentation of the four indentations, the demarcation indicating a position about 3.5 millimeter from the corneal limbus when the device is placed on the eye.

18. The positioning device of claim 17, wherein a demarcation is disposed on the exterior surface of the curved lateral portion adjacent to each indentation of the four indentations.

19. The positioning device of claim 14, wherein the curved lateral portion comprises a roughened underside.

20. The positioning device of claim 14, which comprises martensitic steel, chromium, nickel, molybdenum, carbon, manganese, titanium, acetal copolymer, high-density polyethylene, nylon, polycarbonate, polyethermide, polyphenyl sulfone, polypropylene, acrylonitrile butadiene styrene, acrylic or any combination thereof.

* * * * *